United States Patent
Smith

(10) Patent No.: US 7,199,275 B2
(45) Date of Patent: Apr. 3, 2007

(54) FEED PRETREATING

(75) Inventor: Charles Morris Smith, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 13 days.

(21) Appl. No.: 10/900,617

(22) Filed: Jul. 28, 2004

(65) Prior Publication Data

US 2004/0267066 A1    Dec. 30, 2004

Related U.S. Application Data

(63) Continuation-in-part of application No. 10/807,777, filed on Mar. 22, 2004, now abandoned.

(60) Provisional application No. 60/457,087, filed on Mar. 24, 2003.

(51) Int. Cl.
*C07C 2/66* (2006.01)
(52) U.S. Cl. ..................................... 585/448
(58) Field of Classification Search ................ 585/448
See application file for complete search history.

(56) References Cited

U.S. PATENT DOCUMENTS

| 4,358,362 A | 11/1982 | Smith et al. ............. 208/91 |
| 4,982,052 A | 1/1991 | Nolte ...................... 585/822 |
| 5,030,786 A | 7/1991 | Shamshoum et al. ...... 585/467 |
| 5,744,686 A | 4/1998 | Gajda ....................... 585/823 |
| 5,942,650 A | 8/1999 | Gajda ....................... 585/448 |
| 6,297,417 B1 | 10/2001 | Samson et al. .............. 585/448 |
| 6,313,362 B1 | 11/2001 | Green et al. ................ 585/323 |
| 6,355,851 B1 | 3/2002 | Wu et al. ................... 585/448 |
| 6,617,482 B1 | 9/2003 | Venkat et al. |
| 6,642,407 B2 | 11/2003 | Rao et al. .................. 560/79 |
| 6,753,452 B2 | 6/2004 | Venkat et al. |

FOREIGN PATENT DOCUMENTS

| EP | 0 384 540 | 11/1993 |
| GB | 1 265 687 | 3/1972 |
| WO | WO 01/07383 | 2/2001 |
| WO | WO 02/14240 | 2/2002 |
| WO | WO 2006/032400 | 3/2006 |

OTHER PUBLICATIONS

UOP Sales Brochure, "The Most Efficient Adsorbents", Jan. 1990, 15 pages.
Absract of WO 01/07383, filed Feb. 1, 2001, Uhr et al.
Absract of WO 2006/032400, filed Mar. 30, 2006, Henn et al.

*Primary Examiner*—Thuan Dinh Dang
(74) *Attorney, Agent, or Firm*—Darryl M. Tyus

(57) ABSTRACT

This invention provides for a process for hydrocarbon conversion in which a partially dehydrated hydrocarbon feedstock is contacted with at least two different molecular sieve materials, including a first molecular sieve having a Si/Al molar ratio of less than about 5 and a second molecular sieve having a Si/Al molar ratio of greater than about 5. Also, this invention includes such processes in which such feedstocks are contacted with a first molecular sieve having pores of at least about 6 Angstroms and a second molecular sieve having pores of less than about 6 Angstroms.

7 Claims, No Drawings

FEED PRETREATING

CROSS REFERENCE TO RELATED APPLICATIONS

This application is a continuation-in-part of U.S. patent application Ser. No. 10/807,777 filed Mar. 22, 2004 now abandoned, which application is a nonprovisional application that claims the benefits of U.S. provisional patent application Ser. No. 60/457,087 filed Mar. 24, 2003.

FIELD OF THE INVENTION

The present invention relates to a process for removing substances from a chemical feedstock prior to catalytic conversion in which the catalyst would be impaired by such substances. In particular this invention provides a process for extending the life of catalysts useful for alkylation of aromatics both between regeneration cycles and until replacement is required.

BACKGROUND OF THE INVENTION

Hydrocarbon conversion processes using catalysts are often subject to catalyst regeneration and replacement requirements resulting from "poisoning" of the catalyst by one or more impurities contained in the hydrocarbon feedstock. In many cases, catalyst developments, e.g. to reduce coke-forming and other by-product reactions, have progressed to the stage where "poisoning" by feedstock impurities is the primary reason that catalyst performance deteriorates which forces the catalyst to be replaced or regenerated. Various processes have been developed for removal of such impurities prior to contact with the catalyst.

Alkyl aromatic compounds such as cumene and ethylbenzene are often produced by reaction of aromatics and olefins in the presence of acidic molecular sieve catalysts. Liquid phase operation of aromatics alkylation processes has often been found to result in reduced operating costs as well as fewer undesirable byproducts than earlier vapor phase technologies.

Catalysts that can be used for alkylation of benzene with propylene and also for transalkylation of benzene and polyisopropylbenzenes in liquid phase include zeolite beta, zeolite Y, zeolite omega, ZSM-5, ZSM-12, ITQ-1, ITQ-2, ERB-3, SSZ-25, MCM-22, MCM-36, MCM-49, MCM-56, MCM-58, MCM-68, faujasite, mordenite, porous crystalline magnesium silicates, and tungstate modified zirconia, all of which are known in the art.

Catalysts that can be used for alkylation of benzene with ethylene and transalkylation of benzene and polyethylbenzenes in liquid phase processes include zeolite beta, zeolite Y, zeolite omega, ZSM-5, ZSM-12, ITQ-1, ITQ-2, ERB-3, SSZ-25, MCM-22, MCM-36, MCM-49, MCM-56, MCM-58, MCM-68, faujasite, mordenite, porous crystalline magnesium silicates, and tungstate modified zirconia.

Operation of aromatics alkylation reactions in the liquid phase, especially at relatively low temperatures, has resulted in greater catalyst sensitivity to trace impurities in the feedstock. Various efforts have been made to reduce impurities to extend the catalyst life. Impurities often result in both more frequent catalyst regeneration requirements and reduced ultimate life of the catalyst before replacement is necessary. Catalyst replacement often involves a process shutdown, lost production, and significant costs. A variety of processes have been developed for pretreating chemical feedstocks to remove harmful impurities. These processes include distillation, adsorption, and extraction.

U.S. Pat. No. 6,313,362 (Green), which is incorporated herein by reference, teaches an aromatic alkylation process in which the alkylation product is contacted with a large pore molecular sieve catalyst such as MCM-22 in a liquid phase step to remove impurities prior to liquid phase alkylation. Impurities taught as being removed include olefins, diolefins, styrene, oxygenated organic compounds, sulfur-containing compounds, nitrogen-containing compounds, and oligomeric compounds.

U.S. Pat. No. 4,358,362 (Smith), which is incorporated herein by reference, teaches a method for enhancing catalytic activity of a zeolite catalyst by contacting a feed stream which contains a catalytically deleterious impurity with a zeolitic sorbent. This invention uses a sorbent with a Si/Al ratio greater than 12, 10–12-membered rings, and a Constraint Index between 1 and 12, preferably ZSM-11.

U.S. Pat. No. 5,030,786 (Shamshoum), which is incorporated herein by reference, teaches a process for production of ethylbenzene in which the catalyst lifetime is increased by reducing the concentration of water in the feed to the reactor.

U.S. Pat. No. 5,744,686 (Gajda), which is incorporated herein by reference, teaches a process for the removal of nitrogen compounds from an aromatic hydrocarbon stream by contacting the stream with a selective adsorbent having an average pore size less than about 5.5 Angstroms. The selective adsorbent is a non-acidic molecular sieve selected from the group consisting of pore closed zeolite 4A, zeolite 4A, zeolite 5A, silicalite, F-silicalite, ZSM-5, and mixtures thereof.

A process for preparing alkylated benzenes is taught in U.S. Pat. No. 6,297,417 (Samson), which is incorporated herein by reference. The process includes contacting a benzene feedstock with a solid acid, such as acidic clay or acidic zeolite, in a pretreatment zone at a temperature between about 130° C. and about 300° C. to improve the lifetime of the alkylation and transalkylation catalyst.

U.S. Pat. No. 6,355,851 (Wu), which is incorporated herein by reference, teaches a zeolite-catalyzed cumene synthesis process in which benzene feedstock is contacted with a "hot" clay bed, followed by distillation of the benzene feedstock to separate the benzene from the higher molecular weight materials formed from olefinic poisons during the hot clay treatment, followed by a "cold" clay treatment wherein the benzene distillate is contacted with an ambient-temperature clay. The propylene feedstock is pretreated by contact with an alumina to remove trace sodium compounds and moisture, a molecular sieve to remove water, and two modified aluminas to remove other catalyst poisons. The pretreated propylene and benzene feedstocks are then reacted in the presence of a zeolite catalyst to form cumene without causing rapid degradation of the catalyst's activity.

PCT published application WO0214240 (Venkat), which is incorporated herein by reference, teaches removal of polar contaminants in an aromatic feedstock by contacting it with molecular sieves with pore size greater than 5.6 Angstroms at temperatures below 130° C.

While the processes described above are often successful in improving the life of molecular sieve catalysts, catalyst life is still a problem in commercial applications. The limitations and deficiencies of these prior art techniques are overcome in whole or at least in part by the process of this invention.

SUMMARY OF THE INVENTION

This invention provides for a process for hydrocarbon conversion in which a hydrocarbon feedstock is contacted with at least two different molecular sieves to produce a treated hydrocarbon feedstock. Preferably, the first molecular sieve has a Si/Al molar ratio of less than about 5 and a second molecular sieve has a Si/Al molar ratio of greater than about 5. In another embodiment, such hydrocarbon conversion process includes contacting a hydrocarbon feedstock with at least a first molecular sieve and a second molecular sieve, wherein the first and second molecular sieve have different pore diameters, to produce a treated hydrocarbon feedstock. Preferably, the first molecular sieve has a pore diameter of at least about 6 Angstroms and the second molecular sieve has a pore diameter of less than about 6 Angstroms.

In yet another embodiment, the invention is directed to a process for alkylation of an aromatic hydrocarbon using an aromatic feedstock which has been pretreated using the process described above.

In still yet another embodiment, the invention is directed to a process for alkylation of aromatics using an alkylating agent and an aromatic hydrocarbon which both have been pretreated using the process described above.

DETAILED DESCRIPTION OF THE INVENTION

Molecular Sieve Used for Feedstock Pretreatment

Molecular sieves are porous solids having pores of different sizes including crystalline molecular sieves such as zeolites, as well as carbons and oxides. The most commercially useful molecular sieves for the petroleum and petrochemical industries are crystalline molecular sieves. Crystalline molecular sieves in general have a one-, two-, or three-dimensional crystalline pore structure having uniformly sized pores of molecular scale within each dimension. These pores selectively adsorb molecules that can enter the pores and exclude those molecules that are too large.

Aluminosilicate molecular sieves, also known as zeolites, contain a three-dimensional microporous crystalline framework structure of $[SiO_4]$ and $[AlO_4]$ corner sharing tetrahedral units. Zeolites are generally synthesized by the hydrothermal crystallization of a reaction mixture of silicon and aluminum sources. Other metallosilicate molecular sieves with various metals (such as, for example, gallium, iron, and/or boron) substituted for aluminum in some portion of the crystalline framework are also known in the art.

Molecular sieves are often formed into molecular sieve catalyst compositions to improve their durability and to facilitate handling in commercial conversion processes. These molecular sieve catalyst compositions are formed by combining a molecular sieve with a matrix material and/or a binder. Although the use of binders and matrix materials are known for use with molecular sieves to form molecular sieve catalyst compositions, these binders and matrix materials typically only serve to provide desired physical characteristics to the catalyst composition and have little to no effect on conversion and selectivity of the molecular sieve.

Preferably, the feedstock is at least partially dehydrated prior to pretreatment. While the molecular sieves employed in the pretreatment steps would be capable of dehydration, capacity for adsorption of impurities would be reduced if significant quantities of water adsorbed by the molecular sieve pretreatment material. It is known in the art that drying a hydrocarbon feedstock before pretreating with a molecular sieve having a high Si/Al ratio results in better adsorption of polar compounds. Optimally, the feedstock would be substantially dehydrated prior to pretreatment, with water content on the order of 100 to 200 ppmw or less. This dehydration can be accomplished by any of various methods known in the art, including the use of a separate molecular sieve dehydration step.

In one embodiment of this invention, the first pretreatment step uses a molecular sieve having a Si/Al (silicon-to-aluminum) molar ratio of less than about 5, preferably less than about 2, more preferably between about 1 and about 2. Examples of suitable molecular sieves are Linde type A (LTA) molecular sieves, such as 3A, 4A and 5A, and Linde type X (FAU) molecular sieves such as 13X molecular sieves, and combinations thereof. A description of these molecular sieves, their structures, properties, and methods of synthesis can be found in "Zeolite Molecular Sieves," Donald W. Breck, John Wiley & Sons, 1974, incorporated herein by reference.

The second pretreatment step uses a molecular sieve having a Si/Al molar ratio of greater than about 5, preferably greater than about 10. Suitable molecular sieves include MCM-22, MCM-36, MCM-49, MCM-56, ITQ-1, ITQ-2, PSH-3, SSZ-25, zeolite beta, mordenite, zeolite omega, US-Y, ZSM-5, and combinations thereof.

The entire contents of U.S. Pat. No. 4,954,325, teaching MCM-22; U.S. Pat. No. 5,250,277, teaching MCM-36; U.S. Pat. No. 5,236,575, teaching MCM-49; U.S. Pat. No. 5,362,697, teaching MCM-56; U.S. Pat. No. 6,077,498, teaching ITQ-1; U.S. Pat. No. 6,231,751, teaching ITQ-2; U.S. Pat. No. 4,439,409, teaching PSH-3; U.S. Pat. No. 4,826,667, teaching SSZ-25; U.S. Pat. No. 3,308,069, teaching zeolite beta; U.S. Pat. Nos. 3,130,007 and 4,459,426 and 4,798,816, teaching zeolite Y and its modified forms, such as US-Y; and U.S. Pat. No. 3,702,886, teaching ZSM-5, are incorporated herein by reference. Descriptions of zeolite omega and mordenite are referenced in the "Atlas of Zeolite Framework Types," 5th edition, Ch. Baerlocher, W. M. Meier & D. H. Olson, Amsterdam: Elsevier (2001), incorporated herein by reference. Preferred molecular sieves for use in the second pretreatment step include those having an X-ray diffraction pattern including the following d-spacing maxima 12.4±0.25, 6.9±0.15, 3.57±0.07, and 3.42±0.07.

In another embodiment of this invention, the first molecular sieve has a Si/Al molar ratio of greater than about 5, preferably greater than about 10, and most preferably is MCM-22. The second molecular sieve has a Si/Al molar ratio of less than about 5, preferably between about 1 and about 2, and most preferably is 13X molecular sieve.

In still another embodiment of this invention, a hydrocarbon feedstock is contacted with at least two molecular sieve materials having different pore sizes. Preferably, the first molecular sieve has 12-ring pores (i.e., containing 12 T atoms) with a diameter of at least about 6 Angstroms. Suitable molecular sieves having pore sizes of at least about 6 Angstroms are MCM-22, MCM-36, MCM-49, MCM-56, ITQ-1, ITQ-2, PSH-3, SSZ-25, zeolite beta, mordenite, zeolite omega, US-Y, Linde type X (FAU) molecular sieves, such as 13X, and combinations thereof. Preferably, the second molecular sieve has pores with a diameter of less than about 6 Angstroms. Suitable molecular sieves having pores with diameters of less than about 6 Angstroms include 10-ring pore zeolites such as ZSM-5 and other such medium pore molecular sieves as well as Linde type A (LTA) molecular sieves, such as 3A, 4A, 5A, and combinations thereof.

In still yet another embodiment, the hydrocarbon feedstock is contacted with a first molecular sieve having pores with a diameter of less than about 6 Angstroms, and then a second molecular sieve having pores with a diameter of at least about 6 Angstroms. Suitable molecular sieves having pores with diameters of less than about 6 Angstroms include 10-ring pore zeolites such as ZSM-5 and other such medium pore molecular sieves as well as Linde type A (LTA) molecular sieves, such as 3A, 4A, 5A, and combinations thereof. Suitable molecular sieves having pore sizes of at least about 6 Angstroms are MCM-22, MCM-36, MCM-49, MCM-56, ITQ-1, ITQ-2, PSH-3, SSZ-25, zeolite beta, mordenite, zeolite omega, US-Y, Linde type X (FAU) molecular sieves, such as 13X, and combinations thereof.

In general, molecular sieves preferred for liquid phase pretreatment in either of the pretreatment steps would contain 10-ring pores or larger.

Alpha value is often used as an indicator of the surface acid site activity of a particular molecular sieve. In general, Alpha value tends to increase with increased framework alumina content.

The Si/Al molar ratio referred to may be determined by conventional analysis. This ratio is meant to represent, as closely as possible, the ratio in the rigid anionic framework of the molecular sieve crystal and to exclude aluminum in the binder or in cationic or other form within the channels. Although molecular sieves with Si/Al molar ratios of at least about 5 are useful for the second pretreatment step, it is preferred to use molecular sieves having Si/Al molar ratios greater than about 100.

When synthesized in the alkali metal form, the molecular sieve can be conveniently converted to the hydrogen form, generally by intermediate formation of the ammonium form as a result of ammonium ion exchange and calcination of the ammonium form to yield the hydrogen form. In addition to the hydrogen form, other forms of the molecular sieve wherein the original alkali metal has been reduced, preferably to less than about 1.5 percent by weight, may be used. Thus, the original alkali metal of the molecular sieve may be replaced by ion exchange with other suitable metal cations of Groups I through VIII of the Periodic Table, including, by way of example, nickel, copper, zinc, palladium, calcium, or rare earth metals.

It may be useful to incorporate the above-described crystalline molecular sieve with a matrix comprising another material resistant to the temperature and other conditions employed in the process. Useful matrix materials include both synthetic and naturally occurring substances, as well as inorganic materials such as clay, silica, and/or metal oxides. The latter may be either naturally occurring or in the form of gelatinous precipitates or gels including mixtures of silica and metal oxides. Naturally occurring clays which can be composited with the molecular sieve include those of the montmorillonite and kaolin families, which families include the sub-bentonites and the kaolins commonly known as Dixie, McNamee-Georgia, and Florida clays or others in which the main mineral constituent is halloysite, kaolinite, dickite, nacrite, or anauxite. Such clays can be used in the raw state as originally mined or initially subjected to calcination, acid treatment, or chemical modification.

In addition to the foregoing materials, the molecular sieves employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia, and silica-magnesia-zirconia. The matrix may be in the form of a cogel. The relative proportions of molecular sieve component and inorganic oxide gel matrix, on an anhydrous basis, may vary widely with the molecular sieve content ranging from between about 1 to about 99 percent by weight and more usually in the range of about 5 to about 80 percent by weight of the dry composite.

In general, although it is preferred to conduct the pretreating steps in a flow system, wherein the sorbent particles are in the form of a fixed bed of $1/16$ inch to $1/4$ inch extrudate or pellets, other sorbent shapes and sizes or modes of contact may be employed. The precise conditions selected for the first pretreatment step will be determined by various considerations, including the nature of the feed and the desired degree of refinement, the latter being judged from the observed catalytic consequences of the pretreatment.

It will be obvious to one skilled in the art that parallel or series sets of pretreating units may be used to avoid any need to shut down the process while regenerating or replacing one or both of the pretreatment molecular sieves.

A preferred embodiment of this invention employs spent catalyst for either or both of the pretreatment steps described herein. The term "spent" as used herein will be understood to refer to a molecular sieve which has been used as a catalyst and is no longer being used for catalysis. A spent catalyst will usually be a molecular sieve which has been used and regenerated with a subsequent loss of selectivity and/or activity. Spent catalysts may also include used catalysts which have been replaced for any other reason.

Highly siliceous molecular sieves tend to have an overall lower capacity for adsorption of polar compounds than the same structure containing more framework alumina. In addition, a more highly siliceous molecular sieve will generally show a greater loss of adsorption capacity in the presence of a "wet" as opposed to "dry" hydrocarbon feed. On the other hand, molecular sieves containing higher levels of alumina in their framework structures tend to have higher adsorption capacities and be more hydrophilic than the highly siliceous materials. Therefore, such a molecular sieve will tend to exhibit a higher capacity for adsorption of polar compounds. When a high alumina content molecular sieve is used as an adsorbent with wet hydrocarbon feeds, it will tend to retain more of its dry adsorption capacity. These arguments hold for similar structures in which we can vary the framework alumina content substantially—a principle example is the faujasite structure (FAU) for which 13X molecular sieve represents a high alumina content example and for which US-Y represents a highly siliceous example.

The effect of water on the capacity of all hydrophobic molecular sieves would teach the use of montmorillonite clays as a good choice for adsorbing highly polar compounds from water saturated hydrocarbon feeds. These clays, however, are very weak acids and the potential contaminant must be highly polar in order to be captured on this acid clay. In fact, water saturated hydrocarbon streams are routinely treated over clay to remove strongly basic nitrogen compounds prior to their use in many petrochemical processes.

For reactions that occur at higher temperature in the vapor phase, even highly polar nitrogen compounds will exhibit an adsorption/desorption equilibrium under reaction conditions. In the vapor phase alkylation of benzene with ethylene above about 375° C., as much as 10 ppmw of ammonia can be tolerated in the feed. Even though this level of feed ammonia affects catalyst activity, a lower steady state level of activity is reached and ethylbenzene (EB) can be produced at commercial conditions. Ammonia is a highly polar and basic nitrogen compound, although it is also highly volatile. Since many petrochemical processes run at higher temperatures, it has become common practice to measure the level of basic nitrogen compounds by titration and to control these materials to help manage catalyst activity. If such a strong basic nitrogen compound were present during the liquid-phase alkylation of benzene with ethylene to make ethylbenzene which occurs at much lower temperatures (about 200° C.), it would theoretically be adsorbed on the active sites of the catalyst until the reaction of benzene and ethylene was essentially cut off. In fact, there are a variety of nitrogen compounds with widely varying polarities and basicities. The stronger bases are detected by the titration method discussed above, but the weaker bases are not. With the new lower temperature liquid phase processes, even very low levels of strongly basic nitrogen compounds can have a material impact on catalyst activity over time. In addition, less polar and less basic nitrogen compounds can also impact catalyst activity at lower reaction temperatures exhibiting adsorption/desorption behavior very much like the stronger nitrogen bases at much higher temperatures.

The use of two molecular sieves in series as described above is surprisingly effective for adsorption of a range of polar compounds, and used together can substantially enhance the cycle length for the pretreating system while providing maximum protection for the catalysts used in low-temperature, liquid-phase processing of chemical feedstocks. For example, by choosing to pretreat the feedstock over a "more hydrophilic" lower Si/Al molar ratio molecular sieve in the first instance, and then a "more hydrophobic" higher Si/Al molar ratio molecular sieve in the second instance, removal of a full range of nitrogen compounds can be accomplished, and the high efficiency of the pretreating system to remove even trace levels of these contaminants can be maintained for extended periods.

Alkylation of Aromatic Hydrocarbons

In a further embodiment of the improved alkylation process of the invention, at least one alkylatable aromatic compound, such as benzene, is contacted with a first pretreatment molecular sieve and a second pretreatment molecular sieve as described herein. The treated alkylatable aromatic compound and at least one alkylating agent are contacted under sufficient reaction conditions (preferably liquid phase) and in the presence of a catalyst to provide an alkylated aromatic product comprising at least one alkyl group derived from said alkylating agent. Preferably, a benzene feedstock is contacted with a first molecular sieve, such as 13X molecular sieve, and a second molecular sieve, such as MCM-22, to produce a treated benzene feedstock stream. The treated benzene feedstock stream is contacted with ethylene in the presence of an alkylation catalyst, such as MCM-22, MCM-36, MCM-49 or MCM-56, under suitable alkylation conditions to form ethylbenzene. Optionally, an alkylating agent, such as ethylene, may be contacted with one or more molecular sieves, such as the first and/or second pretreatment molecular sieves, as described herein to form a treated alkylating agent. Often at least one polyalkylated aromatic compound is also produced. Then at least a portion of the polyalkylated aromatic compound(s) and at least one alkylatable aromatic compound can be contacted under sufficient reaction conditions (preferably liquid phase) in a transalkylation section in the presence of a catalyst to convert at least a portion of the polyalkylated aromatic compound(s) to a monoalkylated aromatic compound.

Most aromatic alkylation processes having a liquid phase transalkylation step are suitable for the improvement in accordance with the process of the present invention by the addition of a pretreatment step as described above. For example, U.S. Pat. Nos. 4,962,256; 4,992,606; 4,954,663; 5,001,295; and 5,043,501, each of which are incorporated herein by reference in their entirety for the purpose of describing particular alkylation processes, describe alkylation of aromatic compounds with various alkylating agents over catalysts comprising a particular crystalline material, such as PSH-3 or MCM-22. U.S. Pat. No. 4,962,256 describes preparing long chain alkylaromatic compounds by alkylating an aromatic compound with a long chain alkylating agent. U.S. Pat. No. 4,992,606 describes preparing short chain alkylaromatics by alkylating an aromatic compound with a short chain alkylating agent. U.S. Pat. No. 4,954,663 teaches alkylation of phenols, and U.S. Pat. No. 5,001,295 teaches alkylation of naphthalene. U.S. Pat. No. 5,043,501 describes preparation of 2,6-dimethylnaphthalene. These are a few examples, although certainly not an exhaustive listing, of the types of alkylation processes which may be improved with the present invention.

The term "aromatic" in reference to the alkylatable compounds which are useful herein is to be understood in accordance with its art-recognized scope which includes alkyl substituted and unsubstituted mono- and polynuclear compounds. Compounds of an aromatic character which possess a heteroatom (e.g., N or S) are also useful provided they do not act as catalyst poisons under the reaction conditions selected.

Substituted aromatic compounds which can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups which do not interfere with the alkylation reaction.

Suitable aromatic hydrocarbons include benzene, naphthalene, anthracene, naphthacene, perylene, coronene, and phenanthrene.

Generally the alkyl groups which can be present as substituents on the aromatic compound contain from 1 to about 22 carbon atoms and preferably from about 1 to 8 carbon atoms, and most preferably from about 1 to 4 carbon atoms.

Suitable alkyl substituted aromatic compounds include toluene; xylene; isopropylbenzene; normal propylbenzene; alpha-methylnaphthalene; ethylbenzene; cumene; mesitylene; durene; p-cymene; butylbenzene; pseudocumene; o-diethylbenzene; m-diethylbenzene; p-diethylbenzene; isoamylbenzene; isohexylbenzene; pentaethylbenzene; pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons can also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$. Reformate, especially reformate containing substantial quantities of benzene, toluene, and/or xylene, would also constitute a useful feed for the alkylation process of this invention.

The alkylating agents which are useful in the process of this invention generally include any aliphatic or aromatic organic compound having one or more available alkylating aliphatic groups capable of reaction with the alkylatable aromatic compound, preferably with the alkylating group possessing from 1 to 5 carbon atoms. Examples of suitable alkylating agents are olefins such as ethylene, propylene, the butenes, and the pentenes; alcohols (inclusive of monoalcohols, dialcohols, trialcohols, etc.) such as methanol, ethanol, the propanols, the butanols, and the pentanols; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides, and so forth.

Mixtures of light olefins can also be useful as alkylating agents in the alkylation process of this invention. Accordingly, mixtures of ethylene, propylene, butenes, and/or pentenes which are major constituents of a variety of refinery streams, e.g., fuel gas, gas plant off-gas containing ethylene, propylene, etc., naphtha cracker off-gas containing light olefins, refinery FCC propane/propylene streams, etc., are useful alkylating agents herein.

Typical aromatic alkylation reactions which may be improved the present invention include obtaining ethylbenzene from the reaction of benzene with ethylene, cumene from the reaction of benzene with propylene, ethyltoluene from the reaction of toluene with ethylene, and cymenes from the reaction of toluene with propylene.

The alkylation process of this invention is conducted such that the organic reactants, i.e., the alkylatable aromatic compound and the alkylating agent, are brought into contact with an alkylation catalyst in a suitable reaction zone such as, for example, in a flow reactor containing a fixed bed of the catalyst composition, under effective alkylation conditions. Such conditions include a temperature of from about 0° C. to about 500° C., and preferably between about 50° C. and about 250° C.; a pressure of from about 0.2 to about 250 atmospheres; and preferably from about 5 to about 100 atmospheres, a molar ratio of alkylatable aromatic compound to alkylating agent of from about 0.1:1 to about 50:1, and preferably can be from about 0.5:1 to about 10:1; and a feed weight hourly space velocity (WHSV) of between about 0.1 and 500 hr$^{-1}$, preferably between 0.5 and 100 hr$^{-1}$.

The reactants can be in either the vapor phase or the liquid phase and can be neat, i.e., free from intentional admixture or dilution with other material, or they can be brought into contact with the zeolite catalyst composition with the aid of carrier gases or diluents such as, for example, hydrogen or nitrogen.

When benzene is alkylated with ethylene to produce ethylbenzene, the alkylation reaction may be carried out in the liquid phase. Suitable liquid phase conditions include a temperature between 300° and 600° F. (about 150° and 316° C.), preferably between 400° F. and 500° F. (about 205° C. and 260° C.); a pressure up to about 3000 psig (20875 kPa); preferably between 400 and 800 psig (2860 and 5600 kPa), a space velocity between about 0.1 and 20 WHSV, preferably between 1 and 6 WHSV, based on the ethylene feed; and a ratio of the benzene to the ethylene in the alkylation reactor from 1:1 to 30:1 molar, preferably from about 1:1 to 10:1 molar.

When benzene is alkylated with propylene to produce cumene, the reaction may also take place under liquid phase conditions including a temperature of up to about 250° C., e.g., up to about 150° C., e.g., from about 10C to about 125° C.; a pressure of about 250 atmospheres or less, e.g., from about 1 to about 30 atmospheres; and an aromatic hydrocarbon weight hourly space velocity (WHSV) of from about 0.1 hr$^{-1}$ to about 250 hr$^{-1}$, preferably from 1 hr$^{-1}$ to 50 hr$^{-1}$.

The aromatic feedstock stream may contain impurities such as, for example, olefins, diolefins, styrene, oxygenated organic compounds, sulfur containing compounds, nitrogen containing compounds, oligomeric compounds, and combinations thereof. These impurities or contaminants can deactivate or plug alkylation and/or transalkylation catalysts. These impurities may originate from external feed streams or may be produced in either liquid or vapor phase alkylation reactors, or they may come from both of these sources.

In the process of the present invention these impurities are removed through staged adsorption in a pretreatment step. The removal of these impurities extends the cycle time between catalyst changeouts by preventing poisoning and potential plugging of the valuable catalysts. The operating conditions of the pretreatment step are such that the feed is in the liquid phase.

In some embodiments of the invention, the feedstock stream to be pretreated, i.e. the alkylatable aromatic compound and optionally, the alkylating agent, one or more of which contain some or all of the above-referenced impurities, are brought into contact with the first and second pretreatment molecular sieves, respectively, in a suitable pretreatment zone such as, for example, in a flow reactor containing a fixed bed comprising the molecular sieve, under effective liquid phase conditions to effect the removal of the impurities by adsorption. The alkylatable aromatic hydrocarbon and the alkylating agent may be contacted with the first and/or second pretreatment molecular sieves either sequentially or concurrently. The preferred conditions employed in the pretreatment steps include a temperature of from about 70° F. to about 600° F., and preferably between about 150° F. and about 500° F.; a weight hourly space velocity (WHSV) of between about 0.1 hr$^{-1}$ and about 200 hr$^{-1}$, and preferably from 0.5 hr$^{-1}$ to about 100 hr$^{-1}$; and a pressure between about ambient and about 600 psig. Operating conditions for the pretreatment steps can be any conditions that are appropriate to achieve the preferred inlet conditions for the alkylation reaction.

EXAMPLES

The following examples provide an illustration of the effectiveness of the present invention for alkylation of an aromatic hydrocarbon. A benzene feed was contacted with a conventional 13X molecular sieve in an upflow pretreatment unit. The treated benzene feed and untreated ethylene were contacted with an alkylation catalyst in a reactor under suitable liquid phase alkylation conditions to produce ethylbenzene. The activity of the alkylation catalyst declined by 38 percent after being on stream for 22 days when the benzene feed was pretreated with 13X molecular sieve. Subsequently, an approximately equal volume of 4A molecular sieve was added to the top of the pretreatment unit and downstream from the 13X molecular sieve. After the addition of the 4A molecular sieve, the reactor remained in service using the same alkylation catalyst with no interim regeneration procedures. The pretreatment of the benzene feed with 13X molecular sieve and 4A molecular sieve followed by the alkylation of benzene with ethylene continued to be operated at substantially the same operating conditions for another 22 days. During this time, the activity of the alkylation catalyst showed a further decline of only 2 percent over the second 22 day period, for a total reduction of 40 percent from the initial catalytic alkylation activity. This experiment reveals a substantial and economically significant reduction in the rate of catalyst aging.

In a prophetic experiment comparable to that above, an approximately equal volume of MCM-22 would be placed in a pretreatment unit downstream of 13X molecular sieve. The reactor would remain in service and be operated with no interim regeneration procedures. It is expected that during a test of 22 days in duration, the activity of the alkylation catalyst would show no additional decline. This experiment is expected to reveal a substantial and economically significant reduction in the rate of catalyst aging.

It will be recognized by those skilled in the art that additional pretreatment steps can be combined with the pretreatment process described above, and such combinations are considered to be within the scope of this invention.

I claim:

1. A process for alkylation of an aromatic hydrocarbon stream comprising impurities in which said impurities are removed in a pretreatment system having a first stage, a second stage located downstream of said first stage and a cycle length, said process comprising the steps of:
   (a) contacting the aromatic hydrocarbon stream with a first molecular sieve which is 13X in said first stage of said pretreatment system, to remove at least a portion of said impurities, to produce a partially treated aromatic hydrocarbon stream;
   (b) contacting said partially treated aromatic hydrocarbon stream with a second molecular sieve which is 4A in a second stage of said pretreatment system to remove substantially all of the remaining portion of said impurities, and to produce a fully treated aromatic hydrocarbon stream; and
   (c) contacting said fully treated aromatic hydrocarbon stream with an alkylating agent in the presence of an alkylation catalyst and under alkylation conditions, to produce an alkylated aromatic hydrocarbon stream; and
   wherein said cycle length of said pretreatment system is greater than said cycle length using said first stage of said pretreatment system alone or said second stage of said pretreatment system alone.

2. The process of claim 1, further comprising the step of contacting said alkylating agent of step (c) with a third molecular sieve, to produce a treated alkylating agent, and contacting said treated alkylating agent with said treated aromatic hydrocarbon stream of step (b), to produce said alkylated aromatic hydrocarbon stream of stop (c).

3. The process of claim 1, wherein the first molecular sieve has a Si/Al molar ratio of less than about 5 and the second molecular sieve has a Si/Al molar ratio of greater than about 5.

4. The process of claim 1, wherein the first molecular sieve has a Si/Al molar ratio of less than about 2.

5. The process of claim 1, wherein the second molecular sieve further comprises a molecular sieve selected from the group consisting of MCM-22, MCM-36, MCM-49, MCM-56, ITQ-1, ITQ-2, PSH-3, SSZ-25, zeolite beta, mordenite, zeolite omega, US-Y, ZSM-5, and combinations thereof, any of which may be a spent catalyst.

6. The process of claim 1, wherein the first molecular sieve further comprises a molecular sieve selected from the group consisting of MCM-22, MCM-36, MCM-49, MCM-56, ITQ-1, ITQ-2, PSH-3, SSZ-25, zeolite beta, mordenite, zeolite omega. US-Y, and combinations thereof, any of which may be a spent catalyst.

7. The process of claim 1, wherein the aromatic hydrocarbon is benzene or toluene and wherein the alkylating agent is ethylene or propylene.

* * * * *